United States Patent [19]
Whitton et al.

[11] Patent Number: 6,160,117
[45] Date of Patent: Dec. 12, 2000

[54] CHEMICAL PROCESS

[75] Inventors: Alan John Whitton, Falkirk; Ewan Campbell Boyd, Alloa, both of United Kingdom; Michael Charles Henry Standen; Peter Karl Wehrenberg, both of Daphne, Ala.; Raymond Vincent Heavon Jones, Linlithgow, United Kingdom; Timothy John Doyle, Mobile, Ala.; David Alan Glanville, Edinburgh, United Kingdom

[73] Assignee: Zeneca Limited, United Kingdom

[21] Appl. No.: 09/186,518

[22] Filed: Nov. 5, 1998

Related U.S. Application Data
[60] Provisional application No. 60/090,106, Nov. 6, 1997.

[51] Int. Cl.$^7$ .................. C07D 239/28; C07D 239/30
[52] U.S. Cl. .................................................. 544/319
[58] Field of Search ............................................ 544/319

[56] References Cited

U.S. PATENT DOCUMENTS
4,668,788  5/1987  Beitzke et al. ........................ 544/319

FOREIGN PATENT DOCUMENTS
0 095 637  12/1983  European Pat. Off. .
95 29166   11/1995  WIPO .
95/29166   11/1995  WIPO .

OTHER PUBLICATIONS
Relles H. M. et al. Journal of American Chemical Society., 96: 6469–6475, 1974.
Anonymous. Research Disclosure 690–691, 1996.
Chemical Abstracts, vol. 113, 115234, 1990.
Chemical Abstracts, vol. 113, 97564, 1990.
Chemical Abstracts, vol. 113, 78321, 1990.
Chemical Abstracts, vol. 113, 23838, 1990.
Chemical Abstracts, vol. 112, 55765, 1990.
Chemical Abstracts, vol. 111, 57357, 1989.
Chemical Abstracts, vol. 110, 172946, 1989.
Chemical Abstracts, vol. 110, 95143, 1989.
Chemical Abstracts, vol. 107, 23647, 1987.
Chemical Abstracts, vol. 107, 58962, 1987.
Chemical Abstracts, vol. 103, 215248, 1985.
Chemical Abstracts, vol. 104, 19434, 1986.
Chemical Abstracts, vol. 106, 196369, 1987.
Chemical Abstracts, vol. 105, 43176, 1986.
Chemical Abstracts, vol. 122, 81393, 1995.
Derwent Abstracts, No. 92–309033/38, 1992.
Derwent Abstracts, No. 02846X/02, 1976.
Relles, H.M. et al., Journal of the American Chemical Society, 96:20, Oct. 1974, "Chemical Transformations With Regenerable, Polymer–Supported Trisubstituted Phosphine Dichlorides, The Efficacious Incorporation Of Phosphorus Reagents On Polymer Supports".
Anonymous, Research Disclosure No. 39104, Nov. 1996/691, "Chlorination of Pyrimidines".

*Primary Examiner*—Mukund J. Shah
*Assistant Examiner*—Venkataraman Balasubramanian
*Attorney, Agent, or Firm*—Thomas R. Savitsky

[57] ABSTRACT

4,6-Dichloropyrimidine is prepared by treating 4,6-dihydroxypyrimidine with a chlorinating agent of the formula $R^1R^2R^3PCl_2$ wherein $R^1$, $R^2$ and $R^3$ are independently alkyl or aryl, or one or more of the groups $R^1$, $R^2$ and $R^3$ is linked to a polymer support. Conveniently, the chlorinating agent may be prepared in situ by reacting the corresponding phosphine oxide with phosgene. Thus, in a preferred process, 4,6-dichloropyrimidine is prepared by treating 4,6-dihydroxypyrimidine with phosgene in the presence of a phosphine oxide.

12 Claims, No Drawings

CHEMICAL PROCESS

This application claims benefit to Provisional Application Ser. No. 60/090106, filed Nov. 6, 1997.

The present invention relates to a process for converting 4,6-dihydroxypyrimidine (1) into 4,6-dichloropyrimidine (2) using phosgene. 4,6-dichloropyrimidine is useful as a chemical intermediate in the agrochemical industry. It is especially useful in the preparation of the fungicide, azoxystrobin.

A process for preparing 4,6-dichloropyrimidine from 4,6-dihydroxypyrimidine using phosgene in the presence of a suitable base is described in WO95/29166. Suitable bases include tertiary amines and heterocyclic amines. A process for preparing 2-chloromethyl-4,5,6-trichloropyrimidine from 5,5-dichloro-4,5-dihydro-6-hydroxy-2-trichloromethylpyrimidin-4-one using a chlorinating agent in the presence of a catalyst is described in U.S. Pat. No. 4,668,788. In Example 7, phosgene is used as the chlorinating agent and triphenylphosphine oxide as the catalyst. A similar process is described in EP-A-0095637 for the chlorination of 2,3-dihydroxyquinoxalin-6-carboxylic acid.

According to the present invention there is provided a process for preparing 4,6-dichloropyrimidine comprising treating 4,6-dihydroxypyrimidine with a chlorinating agent of formula $R^1R^2R^3PCl_2$ wherein $R^1$, $R^2$ and $R^3$ are independently alkyl or aryl, or one or more of the groups $R^1$, $R^2$ and $R^3$ is linked to a polymer support.

4,6-Dihydroxypyrimidine (1) can also exist in the tautomeric forms (A) and (B) and references to 4,6-dihydroxypyrimidine include all its tautomeric forms.

The groups $R^1$, $R^2$ and $R^3$ of the chlorinating agent of formula $R^1R^2R^3PCl_2$ are independently alkyl or aryl. Alkyl groups are straight or branched chain and conveniently contain from 1 to 10, especially from 4 to 8, carbon atoms. Examples are methyl, n-butyl and n-octyl. They may also be substituted with, for example, a phenyl ring which itself may be substituted with, for example, one or more $C_{1-6}$ alkyl or $C_{1-6}$ alkoxy groups. Thus, the groups $R^1$, $R^2$ and $R^3$ may be optionally substituted aralkyl, suitably phenyl($C_{1-4}$)alkyl, for example, benzyl. When one or more of $R^1$, $R^2$ and $R^3$ is aryl, the aryl group may be substituted, for example, with one or more $C_{1-6}$ alkyl or $C_{1-6}$ alkoxy groups. Suitably the aryl-group will be phenyl or substituted phenyl. Usually $R^1$, $R^2$ and $R^3$ will be the same. Preferred chlorinating agents are those of the formula $R_3PCl_2$ where R is $C_{1-10}$ alkyl or phenyl and especially triphenylphosphine dichloride, trioctylphosphine dichloride or tributylphosphine dichloride.

One or more of the groups $R^1$, $R^2$ and $R^3$ of the chlorinating agent $R^1R^2R^3PCl_2$ may be linked to a polymer support, for instance, chemically bound to cross-linked polystyrene beads. This may facilitate recovery or reuse of the chlorinating agent. Chlorinating agents of this type and their method of preparation are described in the *Journal of the American Chemical Society* [Oct. 2, 1974] 96:20, pages 6469 to 6475 and the content of this article is incorporated herein by reference. Suitably one of the groups $R^1$, $R^2$ and $R^3$ is a phenyl or benzyl group linked to the polymer support and the other groups are phenyl.

The chlorinating agent of formula $R^1R^2R^3PCl_2$ may be preformed by, for example, the known reaction of the corresponding phosphine oxide with phosgene or the corresponding phosphine with chlorine, and used directly in the process of the invention, or it may be formed in situ. Its in situ formation by the reaction of the corresponding phosphine oxide with phosgene is particularly convenient.

Thus, in a preferred aspect the invention, provides a process for preparing 4,6-dichloropyrimidine comprising treating 4,6-dihydroxypyrimidine with phosgene in the presence of a phosphine oxide.

The phosphine oxide may be a phosphine oxide of the formula $R^1R^2R^3P(O)$, wherein $R^1$ to $R^3$ have the meanings assigned to them above in relation to the chlorinating agent $R^1R^2R^3PCl_2$, or one or more of the groups $R^1$, $R^2$ and $R^3$ is linked to a polymer support in the same way as described above for the chlorinating agent $R^1R^2R^3PCl_2$. Polymer supported phosphine oxides and their method of preparation are also described in the *JACS* [1974] article. Usually $R^1$, $R^2$ and $R^3$ will be the same. Preferred phosphine oxides are those of the formula $R_3P(O)$ where R is $C_{1-10}$ alkyl or phenyl and especially triphenylphosphine oxide, trioctylphosphine oxide or tributylphosphine oxide.

It is preferred that the phosphine oxide:4,6-dihydroxypyrimidine molar ratio is in the range 1:100 to 1:1, especially in the range 1:50 to 1:2, typically 1:20 to 1:3, for example about 1:19.

The amount of phosgene used is preferably from 1 to 5 equivalents of 4,6-dihydroxypyrimidine, suitably from 2 to 4 equivalents and typically from 3 to 4 equivalents. The phosgene may be added continuously or stepwise during the process, but it has been found that better yields are obtained when all or most of the phosgene is present from the beginning.

It has also been found that the quality of the 4,6-dihydroxypyrimidine starting material can have a significant effect on the yield of 4,6-dichloropyrimidine.

It is preferred that the process is carried out in a solvent or mixture of solvents. Suitably, the solvent or mixed solvents are polar and preferably have a boiling point above 80° C., more preferably above 90° C. Nitriles and nitroaromatic solvents are of particular interest, for example, propionitrile, butyronitrile, benzonitrile, acetonitrile, and nitrobenzene. Benzonitrile and nitrobenzene are preferred. It is also envisaged, however, that the reaction may be carried out using less polar solvents or using the end product, 4,6-dichloropyrimidine, as the solvent.

The process is preferably carried out in the temperature range of from 20° C. to 130° C., especially from 90° C. to 120° C., particularly from 100° C. to 110° C. Higher temperatures may be needed with less polar solvents.

In one aspect the present invention provides a process for preparing 4,6-dichloropyrimidine comprising adding phosgene to a mixture of 4,6-dihydroxypyrimidine and a phosphine oxide in a polar solvent having a boiling point above 80° C.

In another aspect the present invention provides a process for preparing 4,6-dichloropyrimidine comprising adding phosgene to a mixture of 4,6-dihydroxypyrimidine and a phosphine oxide in a polar solvent having a boiling point above 80° C., wherein all the phosgene to be used in the process is added at the beginning of the process.

In yet another aspect the present invention provides a process for preparing 4,6-dichloropyrimidine comprising adding phosgene to a mixture of 4,6-dihydroxypyrimidine and a phosphine oxide in a polar solvent having a boiling point above 90° C., and heating the mixture to a temperature below the boiling point of the solvent and in the range of from 90° C. to 120° C.

When a high boiling solvent, such as benzonitrile or nitrobenzene is used, (boiling point above 180° C.), or 4,6-dichloropyrimidine is used as the solvent, the 4,6-dichloropyrimidine may be conveniently isolated from the reaction mixture by distillation. The heal of solvent and catalyst may then be re-used. In this respect, it may be advantageous to use 4,6-dichloropyrimidine as the solvent.

Washing with a caustic solution to remove tarry material may be carried out before or after distillation. This is important if the solvent is to be recycled. Washing before distillation has the advantage of avoiding an initial phosgene stripping stage as excess phosgene will be quenched by the aqueous wash. Separation of the aqueous phase leaves the organic phase for recycling of the solvent and catalyst. When lower boiling solvents are used, the product can be isolated by solvent extraction or by distillation of the solvent and then the product.

The following Examples illustrate the invention. The apparatus used in the following Examples was dried before use, and reactions were conducted under nitrogen using anhydrous conditions. Triphenylphosphine oxide is commercially available, as is dichlorotriphenylphosphorane.

EXAMPLE 1

4,6-Dihydroxypyrimidine (5.18 g at 98% strength; 0.045 mol) triphenylphosphine oxide (3.13 g at 98% strength; 0.011 mol) and nitrobenzene (100 ml) were charged to a 250 ml flanged round bottom vessel fitted with down draft agitator, electric stirrer, thermometer, Drykold/acetone cold trap, pressure equalising dropping funnel, condenser with cold trap, and NaOH scrubber. The system was purged with nitrogen to check for leaks, and Drykold/acetone charged to the cold traps. The 4,6-dihydroxypyrimidine mixture was heated to 60° C. before phosgene (18 g at 99% strength; 0.18 mol) was charged via a dip leg. During the addition a small amount of phosgene started to reflux. The phosgene charge took 20 minutes. The mixture was heated to 105° C. When the temperature was 90° C., a large amount of gassing was seen. This resulted in a high amount of phosgene refluxing to the cold trap. After 20 minutes the reaction mixture was a clear reddish colour. After 40 minutes the gassing rate was very slow, and a small amount of undissolved solid was seen. The reaction mixture was sampled, then held for a further hour, by which time all gassing had ceased. HPLC analysis indicated that the reaction was complete. The reaction mixture was allowed to cool and unreacted phosgene was removed by purging with nitrogen. The reaction mixture was cooled to 30° C. before being drowned out with water (100 ml). This resulted in a two phase mixture. Both phases were sampled and analysed by HPLC. Analysis indicated a quantitative yield of 4,6-dichloropyrimidine.

EXAMPLE 2

The method of Example 1 was repeated except that benzonitrile (100 ml) was used as solvent instead of nitrobenzene. The yield of 4,6-dichloropyrimidine was 97.1%.

EXAMPLES 3–11

4,6-Dichloropyrimidine was prepared from 4,6-dihydroxypyrimidine using the following general procedure.

Phosgene was added over 60–240 minutes to a stirred suspension of 4,6-dihydroxypyrimidine in a catalyst/solvent solution at 100–108° C. During the course of the reaction, the initially yellow suspension gradually darkened becoming first orange and then dark red. This darkening was accompanied by a visible reduction in the amount of suspended starting material. At the end of phosgene addition, the reaction mixture was allowed to stir at the reaction temperature until the reaction became dark red (usually 1–2 hours). Chromatographic analysis was used to monitor the amount of remaining 4,6-dihydroxypyrimidine. At the end of the reaction, the mixture was allowed to cool to room temperature while phosgene was purged from the mixture by sub-surface sparging of nitrogen.

The results are summarised in the following table.

| Example No | Solvent | Temp. (° C.) | Catalyst | Yield | Comments |
|---|---|---|---|---|---|
| 3 | Butyronitrile | 100 | TPPO (25 mol %) | 81% | 3.5 eq. $COCl_2$; 5% loading of DHP |
| 4 | Nitrobenzene | 100 | TBPO (33 mol %) | 94% | 3.5 eq. $COCl_2$; 5% loading of DHP |
| 5 | Nitrobenzene | 108 | TPPO (25 mol %) | 87% | 3.2 eq. $COCl_2$; 5% loading of DHP |
| 6 | Nitrobenzene | 108 | TPPO (25 mol %) | 88% | 4.0 eq. $COCl_2$; 5% loading of DHP |
| 7 | Nitrobenzene | 108 | TPPO (25 mol %) | 86% | 3.3 eq. $COCl_2$; 5% loading of DHP |
| 8 | Nitrobenzene | 108 | TPPO (20 mol %) | 76% | 3.2 eq. $COCl_2$; 12% loading of DHP |
| 9 | Nitrobenzene | 108 | TOPO (15 mol %) | 92% | 3.0 eq. $COCl_2$; 12% loading of DHP |
| 10 | Nitrobenzene | 108 | TOPO (5 mol %) | 96% | 3.3 eq. $COCl_2$; 12% loading of DHP |
| 11 | Nitrobenzene | 108 | TOPO (5 mol %) | 93% | 2.8 eq. $COCl_2$; 12% loading of DHP |

TPPO = triphenylphosphine oxide; TBPO = tributylphosphine oxide; TOPO = triocytlphosphine oxide.

Catalyst levels are expressed as mol % with respect to 4,6-dihydroxypyrimidine.
The yields are derived from an assay of the reaction mixture and represent non-isolated quantities of 4,6-dichloropyrimidine.
DHP=4,6-dihydroxypyrimidine.
% Loading of DHP refers to the weight % of DHP in the reaction mixture before the start of phosgene addition. For example; if the reaction mixture before starting phosgene addition weighed 100 g total and contained 5 g of DHP, this would be indicated as "5% loading of DHP".

EXAMPLE 12

4,6-Dihydroxypyrimidine (0.5 g, 4.46 mmol) was suspended in chlorobenzene (10 ml) and dichlorotriphenylphosphorane (1.44 g, 4.46 mmol; previously prepared by the reaction of triphenylphosphine oxide with phosgene) was added as a solid. The mixture was stirred at 80° C. to 90° C. under a nitrogen atmosphere. Analysis by thin layer chromatography (tlc) of a sample removed after 90 minutes showed some 4,6-dichloropyrimidine formation. However, quite a lot of 4,6-dihydroxypyrimidine remained out of solution. Another quantity of dichlorotriphenylphosphorane (1.44 g, 4.46 mmol) was added and stirring continued for a further hour at 110° C. A cloudy yellow solution was obtained with a solid residue. Analysis by tlc confirmed the formation of 4,6-dichloropyrimidine.

CHEMICAL FORMULAE (in description)

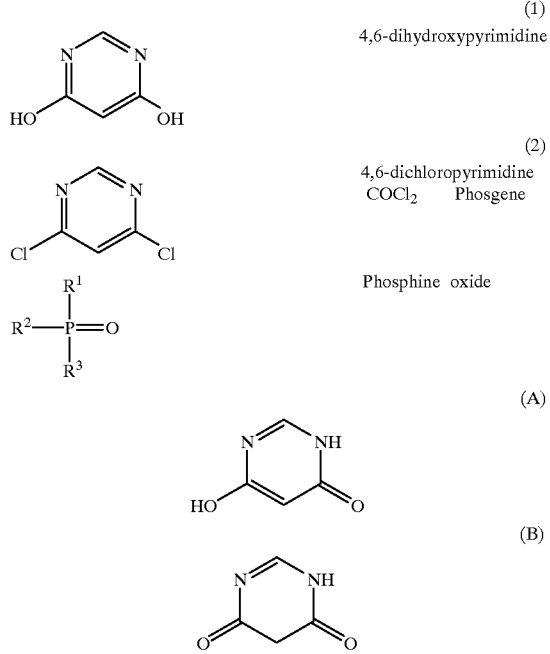

What is claimed is:

1. A process for preparing 4,6-dichloropyrimidine comprising treating 4,6-dihydroxypyrimidine with a chlorinating agent of the formula $R^1R^2R^3PCl_2$ in a polar solvent having a boiling point above 90° C., and heating the obtained mixture to a temperature below the boiling point of the solvent and in the range of from 90° C. to 120° C., wherein $R^1$, $R^2$ and $R^3$ are independently alkyl or aryl, or one or more of the groups $R^1$, $R^2$ and $R^3$ is linked to a polymer support.

2. A process for preparing 4,6-dichloropyrimidine comprising adding phosgene to a mixture of 4,6-dihydroxypyrimidine and a phosphine oxide in a polar solvent having a boiling point above 90° C. and heating the mixture to a temperature below the boiling point of the solvent and in the range of from 90° C. to 120° C.

3. A process according to claim 2 wherein the phosphine oxide has the formula $R^1R^2R^3P(O)$ where $R^1$ to $R^3$ are independently alkyl or aryl, or one or more of the groups $R^1$, $R^2$ and $R^3$ is linked to a polymer support.

4. A process according to claim 2 wherein the phosphine oxide has the formula $R_3P(O)$ where R is $C_{1-10}$ alkyl or phenyl.

5. A process according to claim 4 wherein R is n-butyl, n-octyl or phenyl.

6. A process according to claim 2 wherein the phosphine oxide:4,6-dihydroxypyrimidine molar ratio is in the range 1:100 to 1:1.

7. A process according to claim 2 wherein the phosphine oxide:4,6-dihydroxypyrimidine molar ratio is in the range 1:50 to 1:2.

8. A process according to claim 2 wherein the phosphine oxide:4,6-dihydroxypyrimidine molar ratio is in the range 1:20 to 1:3.

9. A process according to claim 2 wherein the amount of phosgene used is from 1 to 5 equivalents of 4,6-dihydroxypyrimidine.

10. A process according to claim 2 wherein the amount of phosgene used is from 2 to 4 equivalents of 4,6-dihydroxypyrimidine.

11. A process according to claim 2 wherein the amount of phosgene used is from 3 to 4 equivalents of 4,6-dihydroxypyrimidine.

12. A process according to claim 2 wherein all the phosgene to be used in the process is added at the beginning of the process.

* * * * *